United States Patent [19]

Kephart et al.

[11] Patent Number: 6,094,626
[45] Date of Patent: *Jul. 25, 2000

[54] METHOD AND SYSTEM FOR IDENTIFICATION OF GENETIC INFORMATION FROM A POLYNUCLEOTIDE SEQUENCE

[75] Inventors: Thomas W. Kephart, Nashville, Tenn.; Robert W. Cutler, Fort Myers, Fla.

[73] Assignee: Vanderbilt University, Nashville, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/806,280

[22] Filed: Feb. 25, 1997

[51] Int. Cl.$^7$ .............................. G06F 17/18; G06F 17/10; G06F 17/16

[52] U.S. Cl. ......................... 702/179; 702/190; 702/196; 702/197; 702/198

[58] Field of Search .............................. 435/6; 395/908, 395/916, 435, 702

[56] References Cited

U.S. PATENT DOCUMENTS 5,365,455  11/1994  Tibbetts et al. ......................... 364/497

OTHER PUBLICATIONS

Warren Gish and David J. States, Identification Of Protein Coding Regions By Database Similarity Search; *Nature Genetics* vol. 3, pp. 266–272 (Mar. 1993).

Pearson and D.Lipman, Improved Tools For Biological Sequence Comparison, *Proc. Natl. Acad. Sci. USA*, 85:2444–2448 (Apr. 1988).

M. Gates, A Simple Way to Look at DNA, *J. Theor. Biol.*, 119:319–328 (1986).

C. Lawrence; S. Altschu; M. Boguski; J. Liu; A. Neuwald and J. Wootten, Detecting Subtle Sequence Signals: A Gibbs Sampling Strategy For Multiple Alignment, *Science*, vol. 262, pp. 208–214 (Oct. 8, 1993).

E. Hamori, Novel DNA Sequence Representations, *Nature*, vol. 314, pp. 585–586 (Apr. 18, 1985).

R. Guigo; S. Knudsen; N. Drake; and T. Smith, Prediction Of Gene Structrure, *J. Mol. Biol.* 226:141–157 (1992).

V.Solovyev; A.Salamov and C. Lawrence, The Prediction Of Human Exons By Oligonucleotide Composition And Discriminant Analysis Of Spliceable Open Reading Frames, *Proceedings, Second International Conference on Intelligent Systems for Molecular Biology*, (1994).

V. Solovyev and C. Lawrence, Identification Of Human Gene Functional Regions Based On Oligonucleotide Composition, *Proceedings, First International Conference on Intelligent Systems for Molecular Biology*, pp. 371–379, (Jul. 1993).

P. Baldi; Y. Chauvin; T. Hunkapiller; M.McClure Hidden Markov Models Of Biological Primary Sequence Information, *Proc. Natl. Acad. Sci. USA*, 91:1059–1063 (Feb. 1994).

D. Kulp; D. Haussler; M. Reese; and F. Eeckman, A Generalized Hidden Markov Model For The Recognition Of Human Genes In DNA, Journal Not Available.

H. J. Jeffrey, Chaos Game Representation Of Gene Structure, *Nucleic Acids Research*, vol. 18, pp. 2163–2170, No. 8.

C. Dutta and J. Das, Mathematical Characterization of Chaos Game Representation: New Algorithms for Nucleotide Sequence Analysis, Journal Not Available (1992).

C. Burks; E. Myers; W. Pearson, Identifying Features In Biological Sequences: Sixth Workshop Report, Aspen Center for Physics, 29 May–16 Jun., 1995 (Jan. 26, 1996).

M. Burset and R. Guigo, Evaluation Of Gene Structure Prediction Programs, *Genomics*, 34:353–367 (1996).

S.Tiwari; S.Ramachandran; A. Bhattacharya; S. Bhattacharya; and R. Ramaswamy, Prediction Of Probable Genes By Fourier Analysis Of Genomic Sequences, No Journal Citation Available.

E.Uberbacher and R. Mural, Locating Protein–Coding Regions In Human DNA Sequences By A Multiple Sensor––Neural Network Approach, *Proc. Natl. Acad. Sci. USA*, 88:11261–265 (Dec. 1991).

Guigo et al., J. Mol. Bio. 226:141–157, 1992.

Fickett, J.W., Nucleic Acids Research 10(17):5303–5318, 1982.

Shulman et al., Journal of Theoretical Biology 88:409–420, 1981.

Silverman et al., ibid., 118:295–300, 1986.

*Primary Examiner*—Stephanie W. Zitomer
*Attorney, Agent, or Firm*—Waddey & Patterson; Mark J. Patterson

[57] ABSTRACT

A method and system for the identification of genetic information from a polynucleotide sequence is described. Genetic information from a raw polynucleotide sequence is identified by assigning values to nucleotide base changes along the raw polynucleotide sequence and processing these values. Particularly, a distribution of the values of the base changes is generated and the variance from a random distribution of this distribution is calculated by determining the root mean square variance of the distribution. The types of genetic information that can be identified using this system and method include the presence of a protein encoding region, or gene; the number of genes in a given overall polynucleotide sequence; the reading frame for the gene sequence; and tRNA and rRNA sites.

10 Claims, 13 Drawing Sheets

|   | T | G | A | C |
|---|---|---|---|---|
| A | $D_{11}$ | $D_{12}$ | $D_{13}$ | $D_{14}$ |
| C | $D_{21}$ | $D_{22}$ | $D_{23}$ | $D_{24}$ |
| T | $D_{31}$ | $D_{32}$ | $D_{33}$ | $D_{34}$ |
| G | $D_{41}$ | $D_{42}$ | $D_{43}$ | $D_{44}$ |

*FIG. 1a*

$$A = \begin{matrix} 0 & A_{12} & A_{13} & A_{14} \\ -A_{12} & 0 & A_{23} & A_{24} \\ -A_{13} & -A_{23} & 0 & A_{34} \\ -A_{14} & -A_{24} & -A_{34} & 0 \end{matrix}$$

WHERE $A_{IJ} = \dfrac{D_{IJ} - D_{JI}}{2}$

WITH $i, j = 1, 2, 3, 4$

$$S = \begin{bmatrix} S_{11} & S_{12} & S_{13} & S_{14} \\ S_{12} & S_{22} & S_{23} & S_{24} \\ S_{13} & S_{23} & S_{33} & S_{24} \\ S_{14} & S_{24} & S_{24} & S_{44} \end{bmatrix}$$

WHERE $S_{ij} = \dfrac{D_{IJ} - D_{JI}}{2}$

WITH $i, j = 1, 2, 3, 4$

*FIG. 1d*

$$\begin{bmatrix} 0 & -1 & 0 & 1 \\ 1 & 0 & -1 & 0 \\ 0 & 1 & 0 & -1 \\ -1 & 0 & 1 & 0 \end{bmatrix}$$

Table of the Genetic Code

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

METHOD AND SYSTEM FOR IDENTIFICATION OF GENETIC INFORMATION FROM A POLYNUCLEOTIDE SEQUENCE

BACKGROUND OF THE INVENTION

The present invention is directed generally to a method and system for identification of genetic information from a polynucleotide sequence. More particularly, it is directed to a method and system for identifying genetic information from a polynucleotide sequence by calculating the rate of change from one base pair to the next in the polynucleotide sequence and then statistically processing the rate of change data to produce genetic information.

It will be appreciated by one having ordinary skill in the art that due to the speed and sophistication of technological innovation, the genomes of an increasingly larger number of organisms are being sequenced. There is more information in these genetic codes than has yet been experimentally determined; and, identifying information containing regions on sequenced but otherwise unknown genomic material has been the focus of considerable work in the first half of this decade, Burset, et al., Genomics 34: 353–367. Several methods have already been devised to attack this problem at both the DNA and protein sequence level. In addition, sequences with known biological structure can be used in homological comparison with newly sequenced DNA. Computers are the primary tool in this endeavor and more accurate and reliable computational methods are needed to push this work forward.

Once a polynucleotide sequence is generated, it becomes important to identify protein coding regions, or genes, within the polynucleotide sequences. To this end, there have been several attempts to provide systems that predict the location of protein coding regions within polynucleotide sequences. In the last few years several exon identification methods some with gene assembly capabilities have been developed. These include Markov and Hidden Markov models, e.g. P. Baldi, et al., Proc. Nat. Acad. Sci., 91: 1059–1063; statistical methods, e.g. R. Guigó, et al., J.Mol.Biol. 226, 141–157 (1992); homology, e.g. W. Pearson, et al., Proc. Nat. Acad. Sci., 85: 2444–2448; fournier analysis, e.g. S. Tiwari, *Prediction of Probable Genes by Fournier Analysis of Genomic Sequences,* New Delhi preprint 1–22; as well as neural nets, e.g. E. Uberbacher, et al., Proc. Nat. Acad. Sci., 88: 11261–11265; and game theory, e.g. Jeffrey, H. Nucleic Acids Res. 13: 3453–3462. A recent paper by Burset, et al., Genomics 34: 353–367, compared several such methods that predict protein coding regions.

For the most part, the systems described in the prior art attempt to predict the locations of protein in coding regions using the probability that a certain polynucleotide base will appear next in a sequence based on known characteristics that appear in protein coded regions such as start codons, stop codons and the like.

However, none of the systems in the prior art analyze patterns derived from numerical values generated by assigning numerical values to the change of base pairs (i.e., derivative of the sequence) and then adding the numerical values of the change of base pairs over desired sequence length to extract reading frame and directional information. Further, the review article Burset, et al., Genomics 34 353–367, points out the relative inaccuracy and ineffectiveness of currently available gene prediction systems. It points out that currently available products are relatively inaccurate and ineffective with accuracy percentages as low as 30% in some cases. Therefore, among those having ordinary skill in the field, there is dissatisfaction with currently available products.

What is needed, then, is a method and system for identifying genetic information within a polynucleotide sequence that is accurate and reliable. Such a method and system are presently lacking in the prior art.

SUMMARY OF THE INVENTION

A process for producing genetic information from a polynucleotide sequence is described. The process involves the measurement, or determination, of a physical object, i.e., the sequence of a polynucleotide. The polynucleotide sequence is transformed outside of the process of this invention into computer data where the data comprise signals corresponding to bases along the polynucleotide sequence. These signals are then introduced into the process of this invention and the process of this invention causes the physical transformation of the signals representing the bases into signals which are indicative of the presence of a protein encoding region, reading frame of the encoding region, or other genetic information in the polynucleotide sequence. Thus, the process of this invention receives data representing bases on a polynucleotide sequence and converts it into genetic information, e.g. the presence of a gene on a polynucleotide sequence.

Further, this process has the practical and real world application of readily identifying protein encoding regions, reading frames of protein encoding regions, and other genetic information on the polynucleotide sequence. This enables the scientist to identify the location of the gene as a first step in the characterization of a gene. This is much more efficient that current practices, which involve backtracking to a gene from a known biological function. Since the process of this invention identifies genetic information in a polynucleotide sequence rapidly, it will enable genes to be found more readily and thus, their function identified more efficiently. This will enable researchers to more quickly derive therapies based on the knowledge about the function of genes, as well as saving time, man hours and resources that are currently required to identify genes and their biological functions.

More particularly, there is described a method of filtering raw polynucleotide sequence data from a polynucleotide sequence to produce genetic information from the polynucleotide sequence, the method comprising the steps of calculating a rate of change between bases along the polynucleotide sequence and processing said rate of change to produce genetic information. In this method, the step of calculating the rate of change can comprise categorizing base changes within the polynucleotide sequence by assigning a value to each base change and the step of processing said rate of change to produce genetic information can comprise processing the values assigned to each base change within the polynucleotide sequence. The step of processing the values assigned to each base change within the polynucleotide sequence can comprise generating a distribution of the values of the base changes and determining variance from a random distribution of said distribution. In this case, the variance from a random distribution can be determined by calculating the root mean square variance of said distribution.

In the method of the present invention, examples of the genetic information to be identified include the number of protein encoding regions within the polynucleotide sequence; the location of a particular protein encoding region; and a reading frame for a protein encoding sequence within the polynucleotide sequence.

Where the genetic information to be identified comprises the number of protein encoding regions in a polynucleotide sequence, the method of the present invention can comprise calculating the rate of change between bases along the polynucleotide sequence by categorizing base changes within the polynucleotide sequence by assigning a value to each base change. In this case, the step of processing said rate of change to produce genetic information can comprise processing the values assigned to each base change within the polynucleotide sequence; and the processing of the values comprises summing the values assigned to each base change over three base changes and determining whether the sum comprises a statistical significant variation from a random sequence.

Where the genetic information to be identified comprises a reading frame for a protein encoding sequence within the polynucleotide sequence, the method of this invention can comprise the step of calculating the rate of change by categorizing base changes within the polynucleotide sequence by assigning values to each base change using two rate-of-change matrices, an anti-symmetric phase matrix and a symmetric phase matrix; and wherein the step of processing said rate of change to produce the reading frame of a protein encoding region and its direction comprises: processing the anti-symmetric phase matrix by calculating the root mean square variance from the base pair values generated by the anti-symmetric matrix for the protein coding region, said calculating the root mean square variance including calculating an expected statistical deviation to yield a confidence level for the protein encoding region by calculating the magnitude of the elements in the anti-symmetric phase matrix to identify direction of coding sections and to identify tRNA sites; processing a symmetric phase matrix by calculating the RMS variance from a suspected protein coding sequence where the expected statistical deviation is calculated yielding confidence level of protein sequence by calculating the magnitude of the elements to measure the strength of the protein signal; and processing intra-step length comparisons by comparing both symmetric and anti-symmetric step length matrices for different step lengths N mod3; assigning statistical value to step lengths not N mod3, i.e., either N mod3+1 or N mod3+2; and using this information to determine the reading frame.

The present invention can also comprise a program storage device readable by machine, tangibly embodying a program of instructions executable by the machine to perform method steps for identifying genetic information within a polynucleotide sequence, said method steps comprising the method steps set forth in the preceding paragraphs.

The system for filtering raw polynucleotide sequence data from a polynucleotide sequence to produce genetic information from the polynucleotide of this invention comprises a data acceptor for receiving input of raw polynucleotide sequence data; and a filtering unit for filtering the raw polynucleotide sequence data by calculating a rate of change between bases along the polynucleotide sequence and processing said rate of change to produce genetic information. The filtering unit can further comprises a categorizing module for categorizing base changes within the sequence by assigning a value to each base change; and extracting module for extracting genetic information from the polynucleotide sequence by processing the values assigned to each base change within the sequence to extract genetic information from the polynucleotide sequence.

The system of this invention can further comprise a monitor for displaying the genetic information; or a printer for printing out the genetic information. The system can also further comprise a polynucleotide sequence generator operatively connected to the data acceptor. An example of a polynucleotide sequence generator is a DNA sequencing apparatus.

The present invention also comprises an article of manufacture comprising a computer usable medium having computer readable program code means embodied therein for causing the filtering of raw polynucleotide sequence data from a polynucleotide sequence to produce genetic information from the polynucleotide sequence, the computer readable code means in said article of manufacture comprising: computer readable code means for causing a computer to calculate a rate of change between bases along the polynucleotide sequence; and computer readable code means for causing a computer to process said rate of change to produce genetic information. The computer readable code means for causing a computer to calculate a rate of change between bases along the polynucleotide sequence of the article of manufacture of the present invention can further comprise computer readable program code means for causing a computer to characterize base changes within the sequence by assigning a value to each base change. The computer readable code means for causing a computer to process said rate of change to produce genetic information of the article of manufacture of the present invention can further comprise computer readable code means for causing a computer to process the values assigned to each base change within the polynucleotide sequence.

It is an object of this invention to provide a method and system for rapid identification of genetic information from a polynucleotide sequence.

It is a further object of this invention to provide a method and system for filtering raw polynucleotide sequence data from a polynucleotide sequence to produce genetic information from the polynucleotide sequence.

It is yet a further object of this invention to provide a method and system for identifying genetic information by filtering unwanted polynucleotide sequence data from a polynucleotide sequence.

It is a further object of this invention to identify genetic information by determining the rate of change of bases along a polynucleotide sequence.

It is yet a further object of this invention to identify genetic information in a polynucleotide sequence by taking the first derivative of the polynucleotide sequence.

It is still a further object of this invention to provide a method and system for filtering raw polynucleotide sequence data that accurately produces genetic information from the polynucleotide sequence data.

It is yet a further object of this invention to provide a method and system for filtering raw polynucleotide sequence data that shortens the gene identification process.

Other objects and advantages will be apparent from the foregoing detailed description.

BRIEF DESCRIPTION OF THE DRAWINGS

FIG. 1a defines the rate of change matrix D.

FIG. 1b is the most general anti-symmetric phase definition given by the matrix A which is the anti-symmetric part of D.

FIG. 1c depicts a graphical scheme to display base pair sequences and to define the phase (other definitions of phase are determined by permuting the locations of A, C, T, and G in this Figure).

FIG. 1d is the most general symmetric phase definition given by the matrix S which is the symmetric part of D.

FIG. 1e writes the phase of FIG. 1c in the rate of change matrix form wherein the matrix is anti-symmetric.

FIG. 4b is a graphical representation of the phase analysis of the 10 regions spliced end-to-end on the DNA strand complimentary to the strand used in FIG. 4a.

FIG. 11 depicts a table of genetic code.

DESCRIPTION OF THE PREFERRED EMBODIMENT

Definitions

Figure 2:
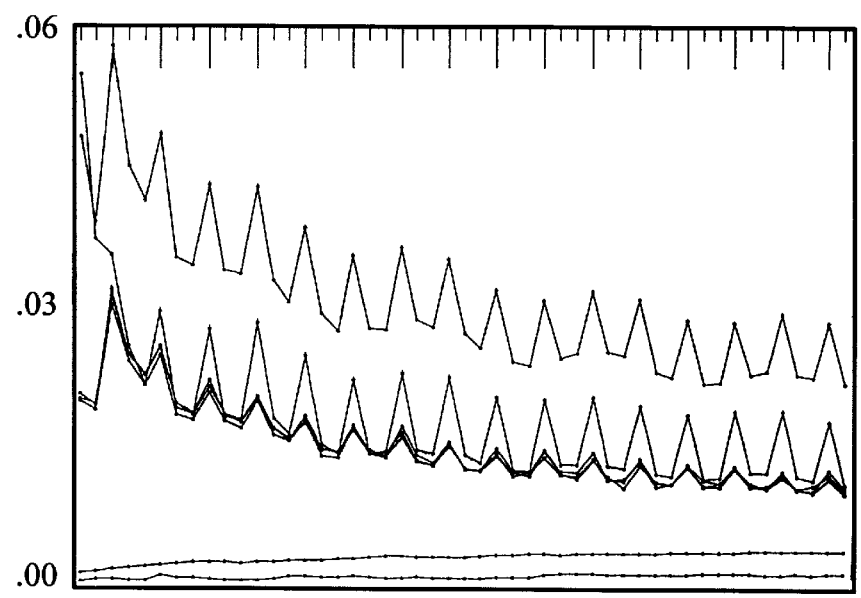
FIG. 2 is a graphical representation of the root mean square variance for, from highest to lowest in graph, mycoplasma genitalium, haemophilus influenzae Rd., as well as yeast chromosomes II, V and XI graphed on the same scale as two random distributions.

As used herein and in the Claims, the following terms are defined to mean the following:

1. Genetic Information

This term is meant to refer to any relevant genetic information that one having ordinary skill in the art may see fit to analyze. Particularly, the genetic information is meant to include genes, protein coding regions, tRNA sites, and other such structures that commonly appear in a polynucleotide sequence. It is also meant to include the reading frame for proteins as encoded by a gene. Genetic information is also meant to include the identification of rRNA sites; determining exon/intron distinctions in eukaryotic DNA sequences; and the number of coding regions within a sequence.

2. Polynucleotide Sequence

This term is meant to refer to both RNA and DNA sequences, entire genomes of organisms, and shorter portions thereof.

3. Base or Nucleotide Base

This term is meant to refer to the nucleotide bases found along a polynucleotide sequence. For example, in a DNA sequence, it is mean to refer to adenine (A); guanine (G); cytosine (C); and thymine (T). For example, in a RNA sequence, it is mean to refer to adenine (A); guanine (G); cytosine (C); and uracil (U). This term can also include mutated and/or genetically engineered variations of nucleotide bases as are known in the art.

4. Root Mean Square Variance

This term is meant to have its standard definition within the field of statistical analysis. That is, the root mean square variance is meant to refer to an amount a distribution of data varies from a random distribution. Particularly, as herein, the data is generated by nucleotide base changes in a polynucleotide sequence.

5. Distribution

This term is meant to have its standard definition under well known statistical analysis techniques. That is, a distribution is a set of data or values generated according to different variables assigned. In this case particularly, one variable is dictated by the polynucleotide sequence in that the value is assigned according to what nucleotide base occurs next in the sequence. Other variables that play a role in setting up the distributions used in producing genetic information as described herein include the "step length", which means the number of nucleotide bases over which the values assigned to each base change are examined.

6. Phase

The term "phase" means rate of change of nucleotide bases along the polynucleotide sequence. Stated differently, the one step length phase is the first derivative of the polynucleotide sequence. Longer step lengths are related to higher derivatives. The graph set forth in FIG. 1a provides the most general scheme for assigning phase at some step length.

7. Raw Polynucleotide Sequence Data

This term is meant to refer to both RNA and DNA sequences, entire genomes of organisms and shorter portions thereof where the data has not been processed from its original source, whether the original source be GENBANK; or a DNA sequencing apparatus; or other database.

8. Strength of Protein Signal

This phrase in meant to refer to the degree the signal varies from a random signal, i.e., the greater the variance from a random signal, the more likely it is that there is a protein encoding sequence present in the polynucleotide sequence.

9. Symmetric Phase

This is an example of a phase definition that can be produced from a matrix such as the exemplary matrix set forth in FIG. 1d.

10. Anti-symmetric Phase

This is an example of a phase definition that can be produced from a matrix such as the exemplary matrix set forth in FIG. 1b.

11. Random Statistical Sequence

Given the four types of base A, T, G and C, we define a random statistical sequence of bases as a sequence generated by choosing bases at random from an equally weighted collection of bases (the probability of choosing any one of the four bases is 25%), and placing them in a sequence in the order in which they are chosen.

12. Random Biological Sequence

If the base in the genome of an organism occur with probabilities PA, PT, PG and PC where PA+PT+PG+PC= 100%, then we define a random biological sequence of bases for this type of organism generated by choosing bases at random from a weighted collection of bases (where the probability of choosing a base A is PA, T is PT, G is PG, and C is PC), and placing them in a sequence in the order in which they are chosen.

13. mod3

A positive integer N taken mod3 is defined by writing N as a sum of 3 times an integer, plus a non-negative remainder that is an integer less then 3, i.e., N=3q+r. Then N mod3 is equal to the remainder r. For example, if N=22, then q=7, and r=1, since 22=3×7+1. Hence 22 mod3=1.

14. $\overline{3}$

In the case of the entire genome, $\overline{3}$+0 is defined as steps whose lengths are divisible by 3 (i.e., 3, 6, 9, 12 . . . ). $\overline{3}$+1 define the steps (1, 4, 7, 10 . . . ). $\overline{3}$+2 define the steps (2, 5, 8, 11 . . . ).

15. $3\overline{3}$

Measuring from the beginning of a base pair sequence that codes for protein, three frames can be defined; we call these $3\overline{3}$+0, $3\overline{3}$+1, and $3\overline{3}$+2. These correspond to reading three bases at a time to code one amino acid. The correct amino acid chain is generated in the so-called reading frame, which is $3\overline{3}$+2. The other two frames do not, in general, correctly encode the protein.

We define the concept of phase as the derivative of the genetic code and analyze DNA for information content from this perspective. We develop a method of 'phase analysis' with which we are able to characterize triplet codons running through complete genomes, various types of coding regions (protein, tRNA), and the reading frame from non-reading frames for proteins. A computer code for identifying protein coding regions is introduced.

The Human Genome Project has focused a great deal of attention on the entire process of gene identification and gene structure prediction. Due to this it has become increasingly clear that all aspects of this activity must become more efficient. To this end we propose a new method of gene identification that holds the promise of some advantages in speed and accuracy. Our approach is based on a method of 'phase analysis' to extract this information. After defining this phase in the space of base pairs (bp), we proceed to demonstrate its relevance in identifying various types of subsequences including protein and tRNA coding regions. We examine the phase structure at three main levels; the entire genome, multiple coding regions, and bp specific coding information. Our phase analysis gives long-range statistical information about DNA sequences as well as exact short-range information, and we find it is possible to distinguish the reading frame from shifted frames.

Various schemes have been suggested to display bp sequences. E. Hamori, Nature 314, 585–586 (1985); M. A. Gates, J. Theor. Biol., 119, 319–328 (1986). The most useful of these for our purposes is that of Gates (M. A. Gates, J. Theor. Biol., 119, 319–328 (1986)). The base pairs $\overline{AT}$ and $\overline{GC}$ correspond to the 2-dimensional axes shown in FIG. 1c with A at (1,0), T at (−1,0), C at (0,1) and G at (0,−1). The phase Φ we are interested in corresponds to rotations in this plane. (For example, the step from A to C is a rotation by π/2, etc.) Rotations by π degrees leave the projected phase unchanged. The full rotation group in the plane is SO(2) [or U(1) for the equivalent description in the complex plane] and is reduced to $Z_4$ in this case. Since bp movement along the DNA sequence occurs in discrete steps, the phase is a local discrete variable. This can be pictured as a discrete gauge theory with the phase for any closed loop of DNA a winding number.

Our method of 'phase analysis' examines the rate of change of bp type along the DNA helix. The phase acquired when moving from one base pair to the next is shown in FIG. 1c where rotations will be scaled by a factor of 2/π (as they will be throughout) for convenience. To expedite the analysis the phase is projected so that ±π/2→±π/2, 0→0,±π→0. One important property of the projected phase definition is that there is a simple exact model for random distributions to compare DNA against since this definition can be fit into a binomial distribution. (The information lost in the projection, ~25% can be recovered using a full quadranomial analysis). For example, starting from any location on a DNA sequence, say A, the 'scaled' phase shift in going to A, T, C, or G is 0, 0, 1 or −1 respectively. For one step length, the number of each value for the phase falls into a binomial distribution corresponding to the coefficients in the polynomial $(x+1)^2$. For n steps, the possible phase changes are:

$$\Delta\Phi=(-n, -n+1, \ldots, n)$$

and again fall into a binomial distribution now generated by $(x+1)^{2n}$. This system leads to an exact mathematical description on multiple length scales.

For an open sequence of DNA, (i.e., not a closed loop of DNA) of total bp length K and a given step length n, there are K−n+1 phases depending on which bp the phase counting is started. If the sequence was purely random then these K−n+1 phases would fall in approximately a binomial distribution. Since we are dealing with finite size sequences, the distribution will not be exactly a binomial but as the random sequence size grows it will tend toward this distribution for random sequences. To examine how much a particular distribution varies from a pure binomial, we can find the variance V(n, l) by subtracting the binomial from the actual distribution.

$$V(n, l) = \frac{\Phi(n, l)}{K - n + 1} - \frac{1}{(n-l)!(n+l)!}$$

where Φ (n, l) is the number of hits of value l on an n step length and this equation defines the normalization of the binomial distribution. The variance V for a pure binomial is zero for all values of n and l. The amount V differs from zero shows how much the actual distribution differs from the pure binomial distribution. The root mean square (RMS) variance of V from a pure binomial for a given step length n is given by:

$$\text{RMS}[V] = \sqrt{\sum_{l=-n}^{n} V(n, l)^2}$$

The bottom two lines in FIG. 2 show the RMS variance of a randomly generated distribution of bps from a pure binomial. The x-axis graphs the step length n, and the y-axis gives the amount the calculated distribution varies from a pure binomial for each step length. The lowest line shows the RMS variance for a 1.2 million bp random distribution and the line above it shows the RMS variance for a random 237 thousand bp random distribution. As expected, the larger the number of base pairs, the closer the distribution is to a purely binomial distribution. This increase is endemic of any limited sample size, but for samples on the order of 200 thousand bps and larger it does not affect the results to be presented. The small increase in the RMS variance of a particular distribution as the step length increases is due to the decreasing number of phase counts given by K−n+1. Now that a clear determination of a random distribution has been made, the variance for several distinct species of DNA can be understood.

In Example 1 the gross properties of complete genomes and chromosomes are considered. In Example 2 the focus is on a single organism (MG), wherein multiple coding regions of particular types (protein, tRNA) are examined. Example 3 examines single coding regions with particular attention given to the reading frame for proteins and the coding algorithm used to encode information onto DNA.

EXAMPLE 1

The Entire Genome

Figure 12:
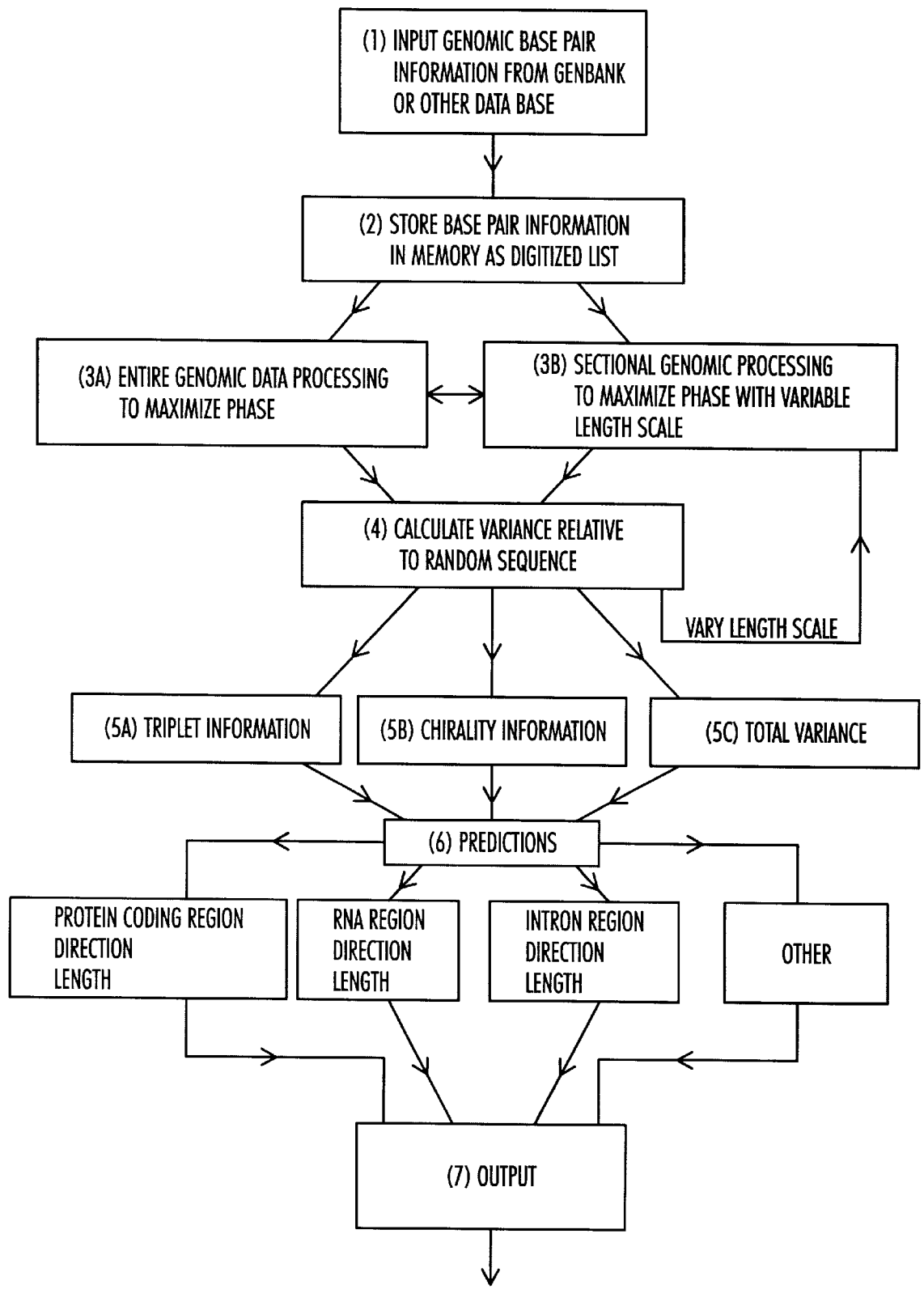
FIG. 12 is a flow chart of the general methods used to obtain genetic information from raw polynucleotide sequence data, in accordance with the present invention.

Several complete and partial genomes have been examined. Haemophilus Influenzae Rd Science 269, 496–512 (1995); Mycoplasma Genitalium, Fraser et. al., Science 270, 397–403 (1995), as well as the Yeast Chromosomes II,V, and XI. (Due to the large number of authors and sources, reference is made to GenBank where said information is stored.) These complete sequences have between 570 thousand bps for yeast V and 1.8 million bps for the Flu. There are several ways to examine the data; on the grossest scale, the entire genome can be phase analyzed. Remarkably at this level, the RMS variance from a pure binomial for each of these sequences has a similar behavior over multiple step lengths. A flow chart describing Example 1 is depicted in FIG. 12. For Example 1, the particularly relevant steps of the flow chart include step 3a and step 5c.

FIG. 2 shows the RMS variance for each of these genomes graphed on the same scale with the random distributions. In FIG. 2, the x-axis is the number of base pairs n counted over and the y-axis is the root mean square variance from a pure binomial of size $2^{2n}$. The genomes displayed from the top are MG, Flu, Yeast Chromosome II,V,XI, a random distribution on 237 k base pairs, and a random distribution on 1.2M base pairs. The spiked behavior shows that there is a buildup of phase for step lengths divisible by three. Phase analysis done on particular regions of the DNA show that this spiked behavior is due to phase triplets in protein coding regions. Since this RMS variance analysis sums over the entire genome including non-coding regions, as well as off frame phases within coding regions, the triplet behavior is somewhat washed out. As we will see in the next section, when looking at particular coding regions, the deviance from a pure binomial is approximately an order of magnitude greater than the variance shown in FIG. 2.

Figure 3A:
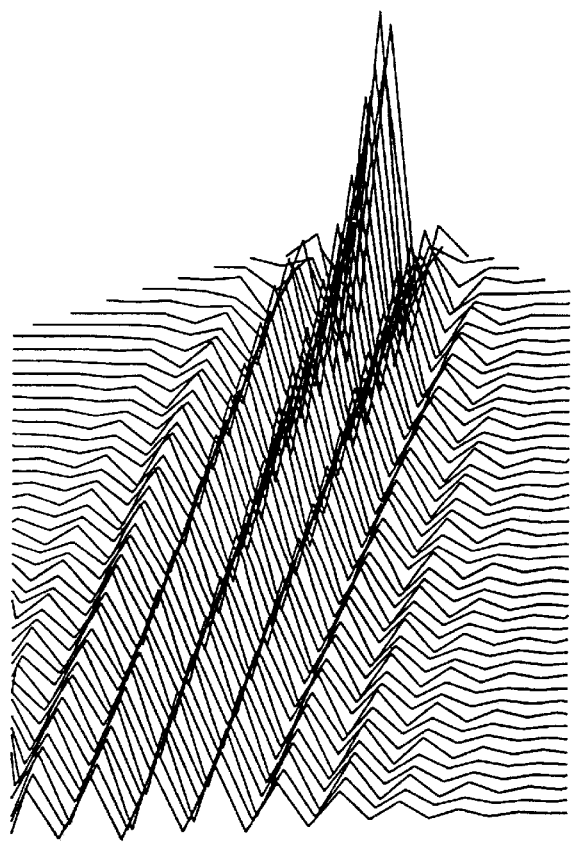
FIG. 3a is a graphical representation of the variance for all step links in the genome of mycoplasma genitalium.
Figure 3B:
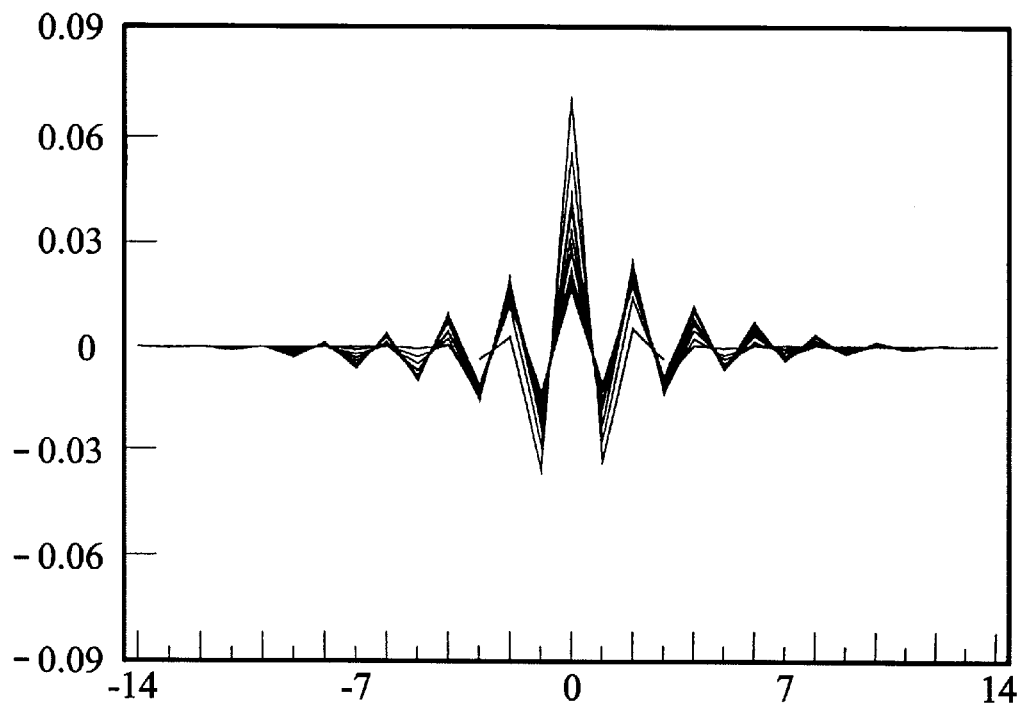
FIG. 3b is a graphical representation of the variance for the mycoplasma genitalium genome at a step length of $\overline{3}+0$ steps.
Figure 3C:
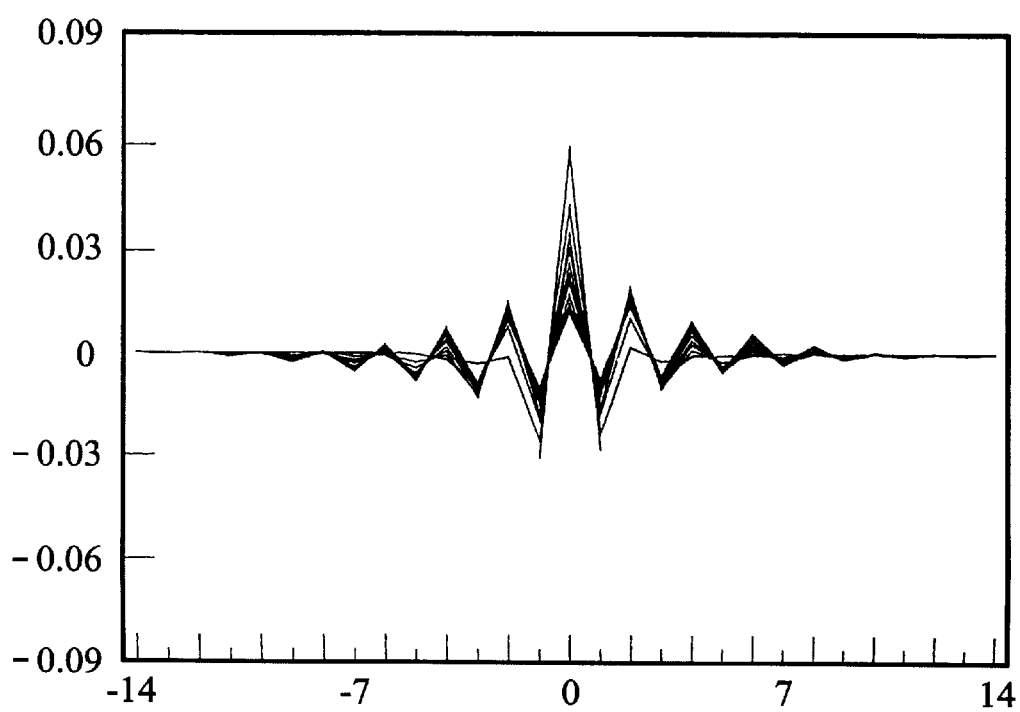
FIG. 3c is a graphical representation of the variance for the entire genome of mycoplasma genitalium for step links $\overline{3}+1$ step link.
Figure 3D:
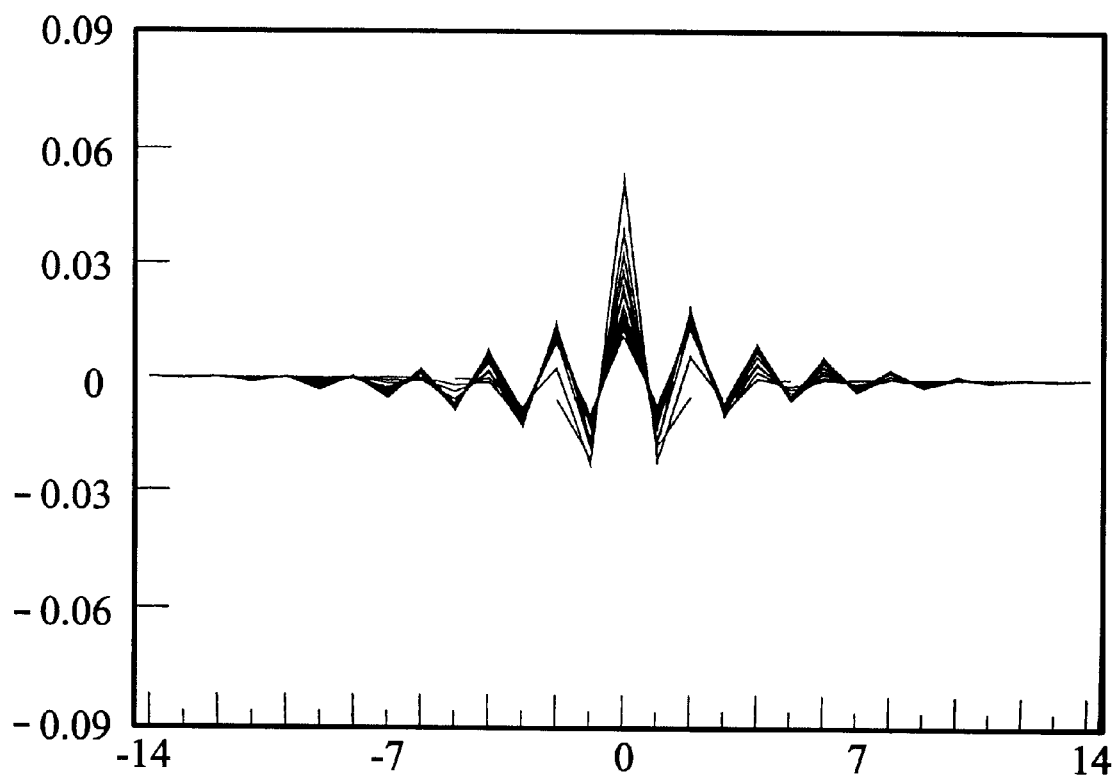
FIG. 3d is a graphical representation of the variance for the entire genome of mycoplasma genitalium for step links $\overline{3}+2$ step links.

In FIGS. 3a, 3b, 3c and 3d, the x-axis is the phase step for all step lengths and the y-axis is the amount each phase differs from a pure binomial. These four figures graph the phase analysis for the entire genome of Mycoplasma Genitalium (MG). FIG. 3a graphs a 3-D depiction of FIGS. 3b, 3c, 3d to show how the phase distribution changes as the step length is increased. FIG. 3b graphs the $\overline{3}$+0 steps (i.e. 3,6,9, . . . ) while FIGS. 3c,d graph the $\overline{3}$+1 and $\overline{3}$+2 step lengths respectively. Note the $\overline{3}$+0 steps are markedly higher than either other step length.

Although the RMS variance shows the total variation from a pure binomial distribution for each step length, the particular distributions of phases is lost. Since the following analysis is similar for each of the genomes we have examined, we will focus on Mycoplasma Genitalium (MG). For the complete genome of MG the variance V for all step lengths is shown in FIG. 3a. V is graphed to show how the particular distribution of phases changes as the step length increases. The behavior is very smooth over all step lengths, but there are in fact three distributions within this graph. FIG. 3b graphs the $\overline{3}$+0 steps (i.e. 3,6,9, . . . ) while FIGS. 3c and 3d graph the $\overline{3}$+1 and $\overline{3}$+2 step lengths respectively. All of these graphs are roughly symmetrical about zero phase and have an overabundance of even phases and an underabundance of odd phases. The behavior at all step lengths is similar but in FIG. 3b the overabundance of even and underabundance of odd phases is markedly greater than either the $\overline{3}$+1 or $\overline{3}$+2 step lengths which are nearly identical. The behavior of V in every genome we have examined is similar to the variance of the complete genome of MG. Minor differences such as reversal of the number of zero to plus or minus 1 phases at the 1 step length for human T-cell (while all other step lengths are not reversed) show that the phase information is not identical throughout all species but is remarkably similar.

EXAMPLE 2

Multiple Coding Regions

Figure 4A:
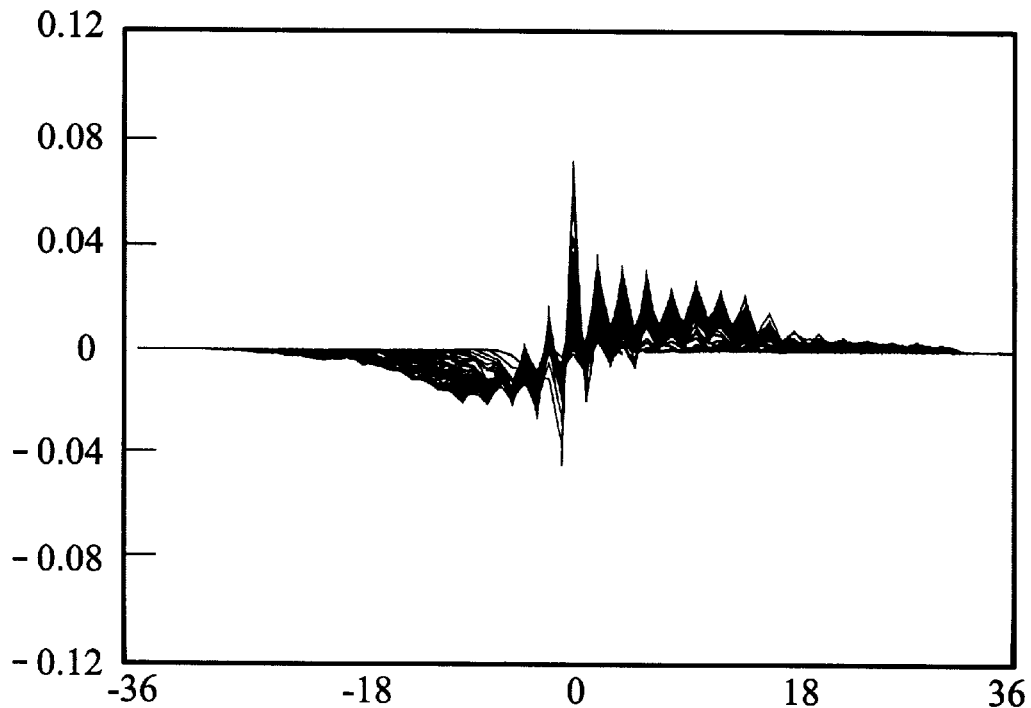
FIG. 4a is a graphical representation of the phase analysis of a strand of mycoplasma genitalium DNA that includes 10 codon regions spliced together.

To this point our analysis is still at the level of entire chromosomes. Let us now shift the focus down to multiple coding regions which will reveal several important facts about how information is coded onto the DNA helix. It was stated above that the enhancement at step lengths divisible by three is due to phase triplets in protein coding regions. To examine this we took ten coding regions from a strand of MG DNA and spliced these sections end to end. This subset of the MG complete genome was phase analyzed and FIG. 4a is the result. The same spiky behavior seen in FIG. 3b is present in this sample but the positive to negative phase symmetry is gone. For coding sections on this strand, there is a general and significant buildup of positive phase in the protein coding region, with a total underabundance of negative phase. At the same time there is an overabundance of even phase and an underabundance of odd phase throughout the entire region. A flow chart describing Example 2 is depicted in FIG. 12. For Example 2, the particularly relevant steps of the flow chart include step 3b and step 5b.

Figure 4B:
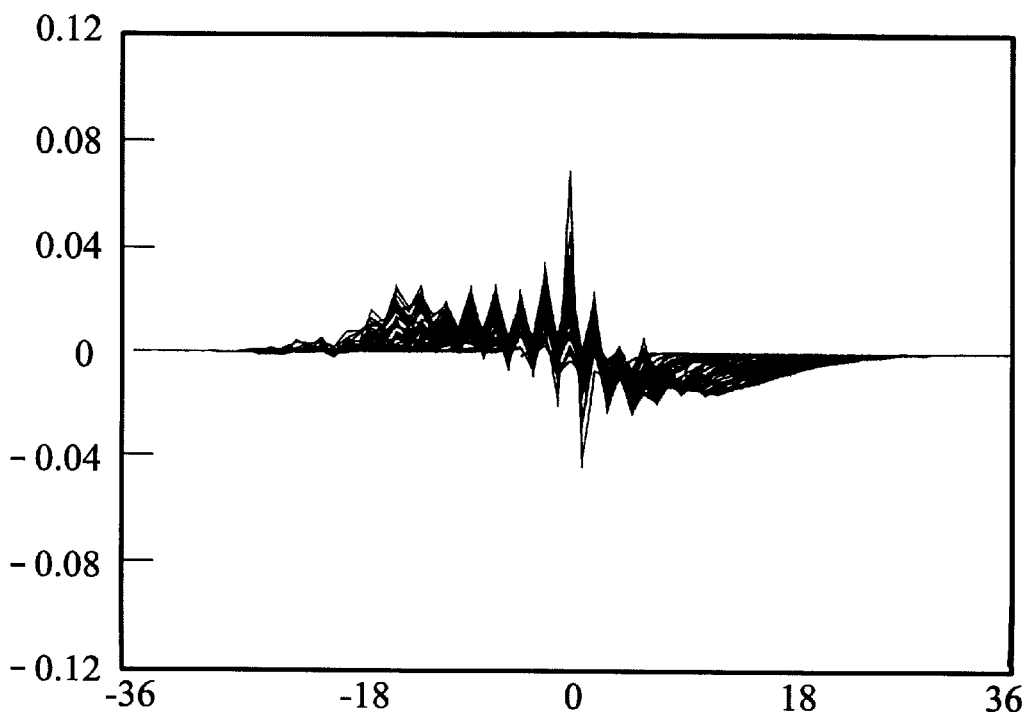

In FIGS. 4a and 4b, the x-axis is the phase step for all step lengths and the y-axis is the amount each phase differs from a pure binomial. FIG. 4a graphs the phase analysis on 10 proteins spliced end to end that code on the forward strand of MG. FIG. 4b graphs the same data on 10 proteins spliced end to end that code on the second strand of MG. Note the reversal of phase between these two graphs that shows the phase coding signature. Also note the general shape indicative of protein coding sections.

At the level of multiple coding regions, it is also possible to examine proteins coding on the conjugate DNA strand. The bp information that encodes these proteins is stored in reverse order by conjugate bases on the first DNA strand. To analyze these coding regions we calculate the phase by reading the first strand in the forward direction, which is opposite the direction in which the protein is coded on the conjugate strand. Conjugation of the bp sequence does not alter the phase but reading in the reversed direction introduces a minus sign. If regions on the first strand, complementary to coding regions on the conjugate DNA strand, show an identical but reversed signature with respect to the phase, then the coding algorithm built into DNA actively stores this phase information. To test this we took ten protein coding regions on the conjugate strand and spliced them end to end. The results of this phase analysis are shown in FIG. 4b. This phase information has the reversed signature expected for the phase information to be actively coded.

Another type of single coding segment is tRNA. In MG there are 32 known tRNA sites, 15 of which occur on one DNA strand. After splicing these 15 regions into one file, the results shown in FIG. 5a were generated, this shows that the distribution of phases is mainly shifted in one direction. FIG. 5c shows how the phases evolve as the step length is increased, and is a 3D rendering of the information in FIG. 5a. The phase analyzed data for the 17 sections on the second strand has the reversed phase signature expected to complement the first 15 as seen in FIG. 5b.

Figure 5A:
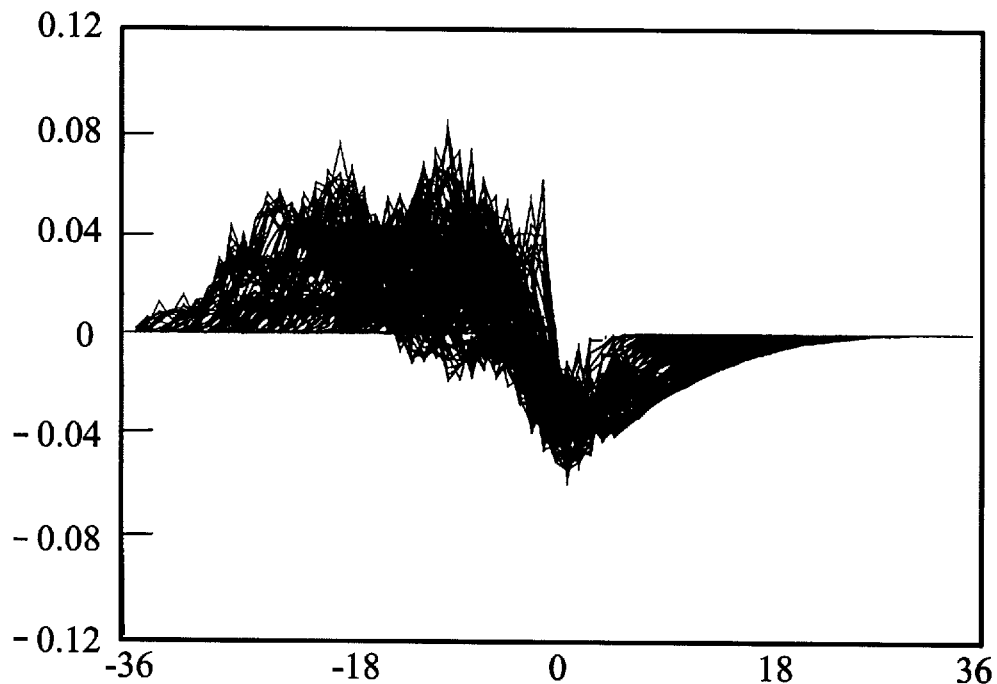
FIG. 5a is a graphical representation of phase analysis of 15 tRNA sites of mycoplasma genitalium spliced into one file.
Figure 5B:
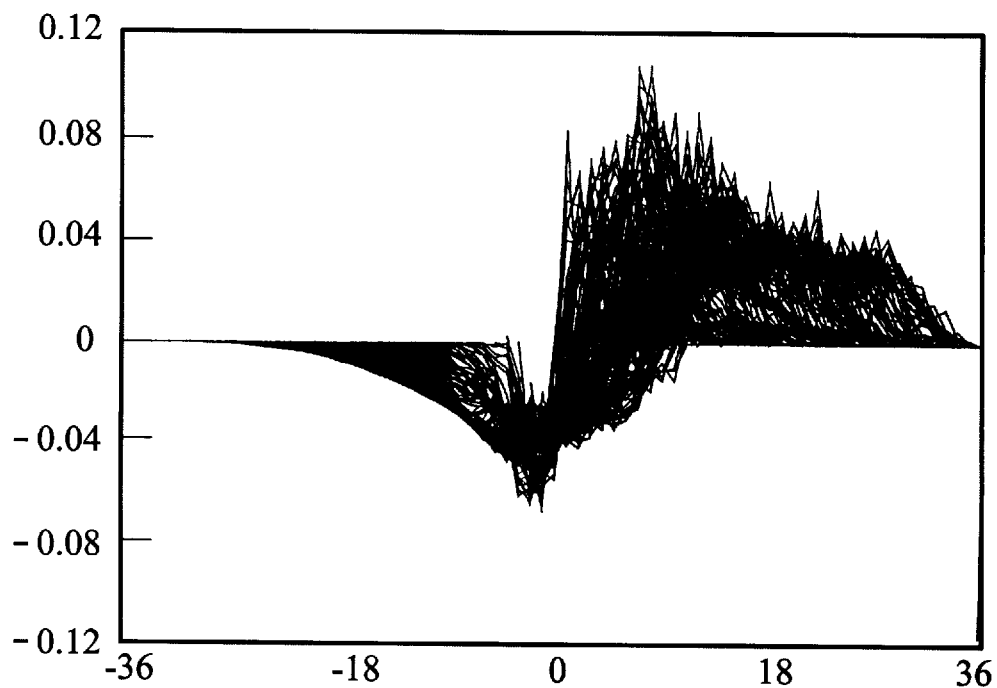
FIG. 5b is a graphical representation of the phase analysis for the 17 tRNA sites on the second strand of the mycoplasma genitalium genome.
Figure 5C:
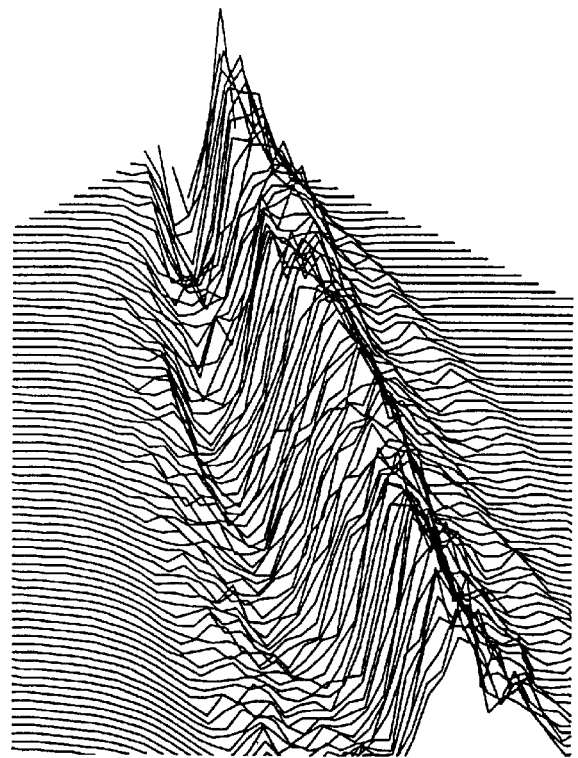
FIG. 5c is a three-dimensional rendering of the information in FIG. 5a, showing how the phases evolve as the step length is increased.

In FIGS. 5a, 5b and 5c, the x-axis is the phase step for all step lengths and the y-axis is the amount each phase differs from a pure binomial. FIG. 5a graphs the phase analysis on the 15 tRNAs spliced end to end that code on one strand of MG. FIG. 5b graphs the same data on the 17 tRNAs spliced end to end that code on the second strand of MG. FIG. 5c graphs FIG. 5b three dimensionally to show how the phase information changes as the step length is increased. Note the reversal of phase between these two graphs that shows the phase coding signature. Also note the general shape indicative of tRNA coding sections (a large buildup of phase in one direction).

Figure 6:
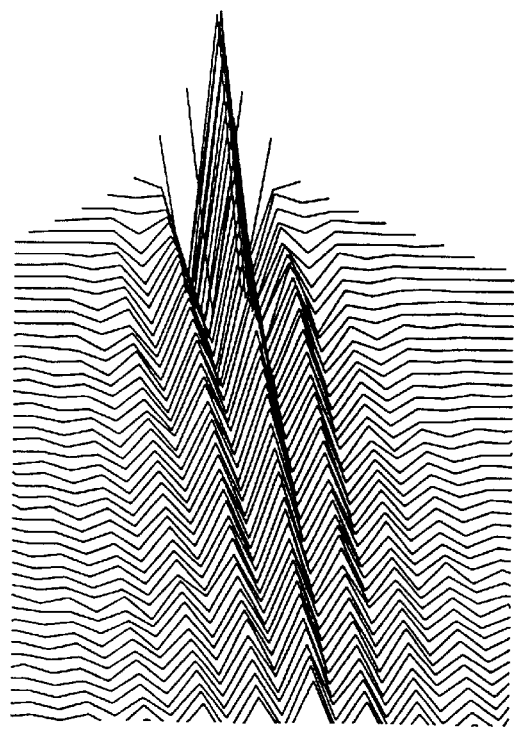
FIG. 6 is a graphical representation of how the phase distribution in the human T-cell beta locus gene varies as the step length is increased.

The greatest amount of bp information is stored when there is a non-zero change in phase between two bps since this precisely sets the second bp. The genomes examined so far have an overabundance of zero phase and an underabundance of odd phase on one step length. In the Human T-Cell beta locus gene, L. Rowen et. al., unpublished (1994); J. L. Slightom, Genomics 20 2, 149 (1994), the opposite is true. There is a complete reversal in the number of zero to odd phases on a one step length. FIG. 6 shows how the phase distribution varies as the step length is increased. In FIG. 6, the graph is a 3-D depiction of the phase data for Human T-Cell Beta locus. Note the similar behavior to FIG. 3d with an inverted distribution on one step length. In spite of the reversal of number of odd versus 0 phases, the distribution on all other step lengths is similar to the results presented above. Phase analysis has been conducted on step lengths up to 400 bps and only the 1 step length shows this reversed signature. This implies that there is an inherent algorithm that produces this spiky behavior that is not dependent on the numbers of one step length phases. Partly this behavior is due to a phenomenon we call 'phase locking' which we will examine in the next section.

There are several general points about the RMS variance that can be used to gain more information about a particular genome. For genomes with larger numbers of coding regions, there will be a greater correlation of the triplet behavior on all step lengths divisible by three (i.e. the spiky behavior at every third step length is enhanced when there are more coding regions). Therefore the enhancement at $\bar{3}+0$ step lengths over $\bar{3}+1$ and $\bar{3}+2$ step lengths gives a measure of the number of coding regions. Unfortunately, determining this percentage experimentally is a difficult task so percentages are not accurately known for all genomes, but MG is reported to have 88% coding regions whereas human DNA is generally under 5%. Once a determination of coding percentages has been made, it should be possible to get a direct correlation between this enhancement and the total number of coding regions. This would be useful since the phase information for new genomes could be gathered within the space of a few minutes and the coding percentages could be determined from this.

Our analysis of long-range effects of multiple coding regions has shown large scale effects like triplet phase coding. This long range structure is remarkably similar for widely varying genomes and extends down to the multiple bp regime with the slight proviso seen in the Human T-cell reversed signature at the one step length. It would be ideal if all the structure seen in the long-range effects translated directly down to small single coding regions, but such is not the case. However by shifting our perspective slightly, phase analysis can give results for single protein coding regions.

EXAMPLE 3

Single Coding Regions

Figure 7A:
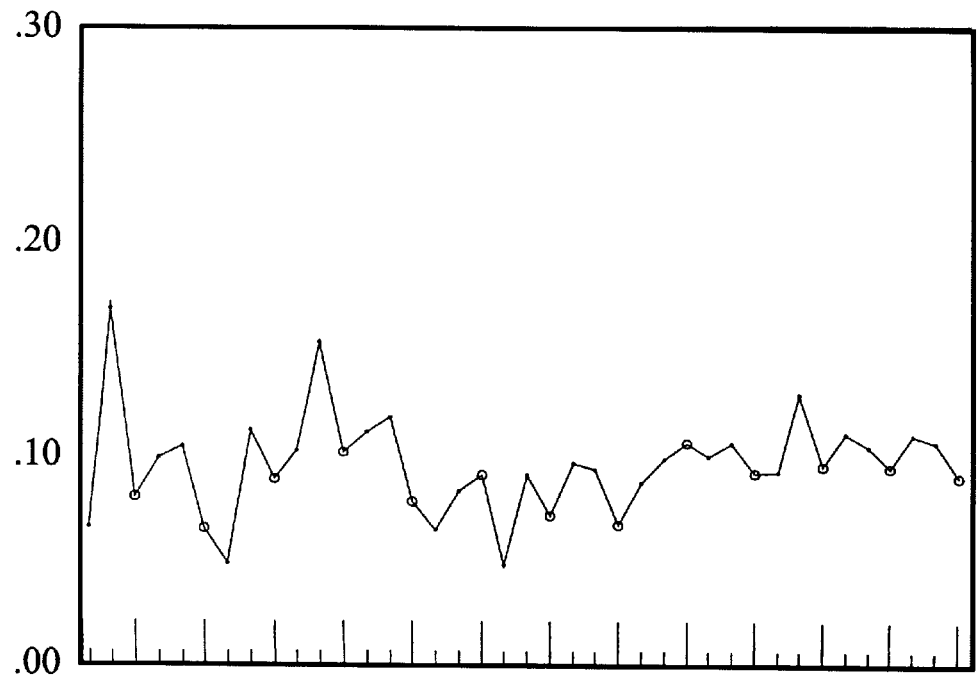
FIG. 7a is a graphical representation of the root mean square variance for the $3\overline{3}+0$ frame for the first coding region $P_1$ of the mycoplasma genitalium genome.

For the results presented above, the phases are taken from each bp site in the sequence. On the scale of single coding regions, the two off frame phases overwhelm the on frame phases so the RMS variance for all these phases together does not give dramatic results. Instead of counting all three frames together, three distributions can be made for bps starting in the $3\bar{3}+(0,1,2)$ frames (where the $3\bar{3}$ frames are not to be confused with the $\bar{3}$ notation for step lengths). When this analysis is done, the three distributions can be examined and the on frame distribution is enhanced at step lengths divisible by three. For example, in MG the first coding section $P_1$ starts on bp 1026 and goes to bp 1829. The RMS variance for the $3\bar{3}+(0,1,2)$ frames are shown in FIGS. 7a,b,c. A flow chart describing Example 3 is depicted in FIG. 12. For Example 3, the particularly relevant steps of the flow chart include step 3b and step 5a.

Figure 7B:
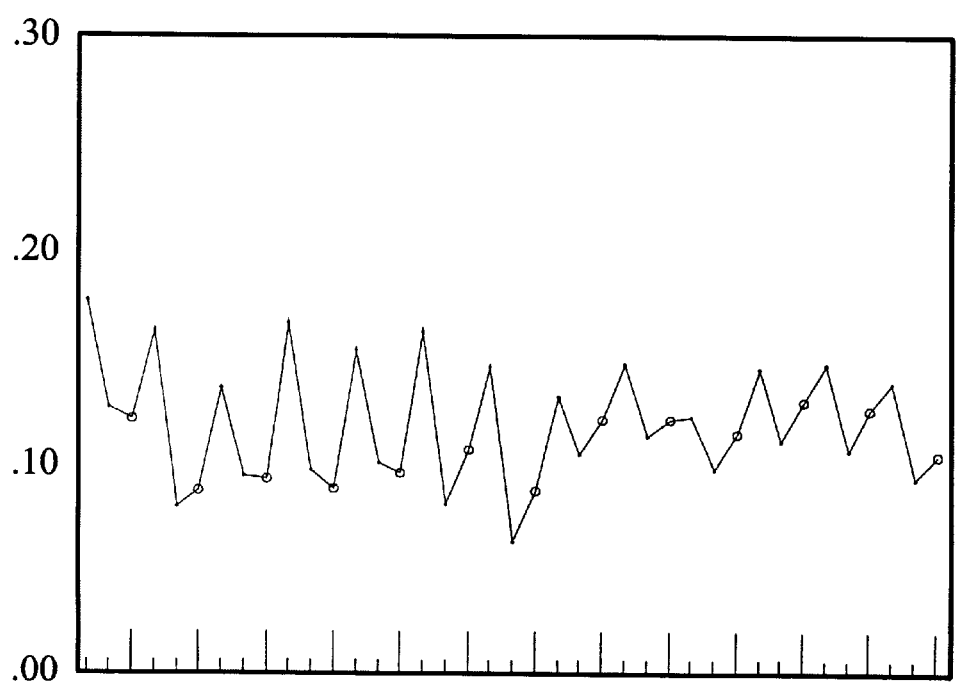
FIG. 7b is a graphical representation of the root means square variance for the $3\overline{3}+1$ frame for the first coding region $P_1$ of the mycoplasma genitalium genome.
Figure 7C:
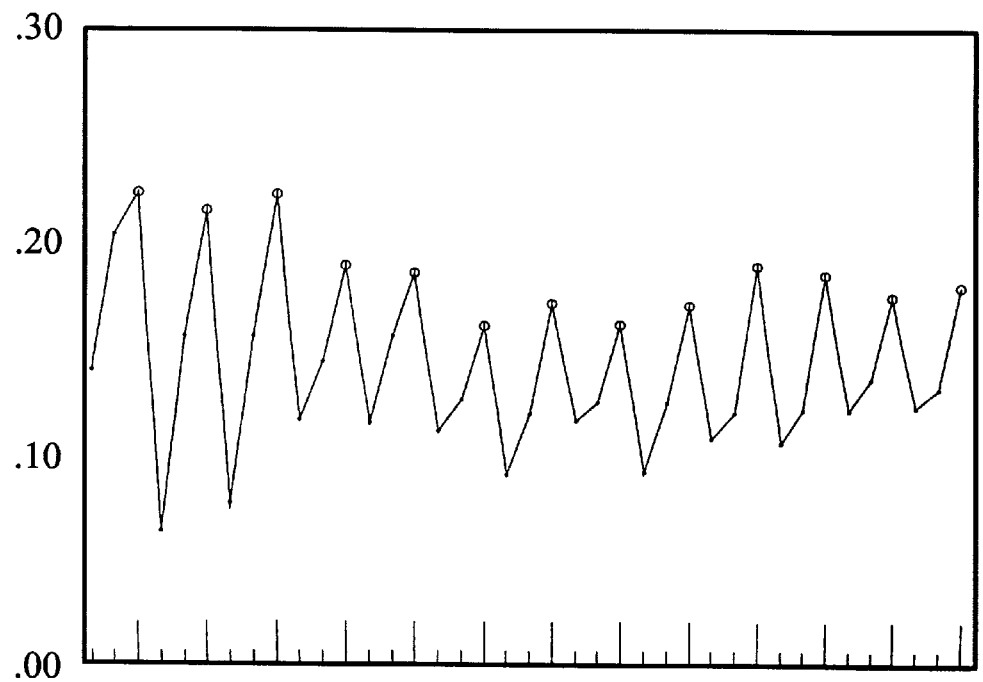
FIG. 7c is a graphical representation of the root means square variance for the $3\overline{3}+2$ for the first coding region $P_1$ of the mycoplasma genitalium genome.

In FIGS. 7a, 7b and 7c, the x-axis is the number of base pairs n counted over and the y-axis is the root mean square variance from a pure binomial of size $2^{2n}$. These graphs display phase information for a single protein in MG, with step lengths divisible by three circled. FIG. 7a graphs the $\frac{3}{\bar{3}}+0$ frame (i.e. 3,6,9, . . . ) while FIGS. 7b and 7c graph the 3$\bar{3}$+1 and 3$\bar{3}$+2 frames respectively. Note FIG. 7c shows the reading frame of the protein because of the enhancement at all step lengths divisible by three.

In FIGS. 7a, 7b and 7c, the value of the RMS variance for every third step length is circled so the behavior can be easily seen. Note that the scale for this single coding region is five times larger than in FIG. 2. In general as seen in FIG. 7c the reading frame is the 3$\bar{3}$+2 frame. As in the long-range analysis, all step lengths divisible by three spike away from a pure binomial. This implies that when a bp sequence that codes amino acids is being stored on the DNA, the first phase step goes from the last bp in the preceding triplet to the first bp in the new triplet. Knowing this, it is possible to examine stretches of DNA and extract the reading frame. The current standard scheme to determine the reading frame is to match bps of a sequence to a known protein. We expect all proteins can be systematically mapped using phase analysis and known protein information can be checked against these results.

The analysis to this point takes a given sequence of DNA and displays the phase properties of the sequence by relating the actual distribution to a random binomial distribution. The last level of analysis examines how phase structures are actually encoded onto the DNA helix. The long-range and short-range behavior examined above suggests how this encryption of information onto the DNA helix occurs. We will now examine how the coding algorithm works and how it has the freedom to code the complex behavior already presented. Finally a mechanism for this encryption algorithm will be examined.

Figure 8:
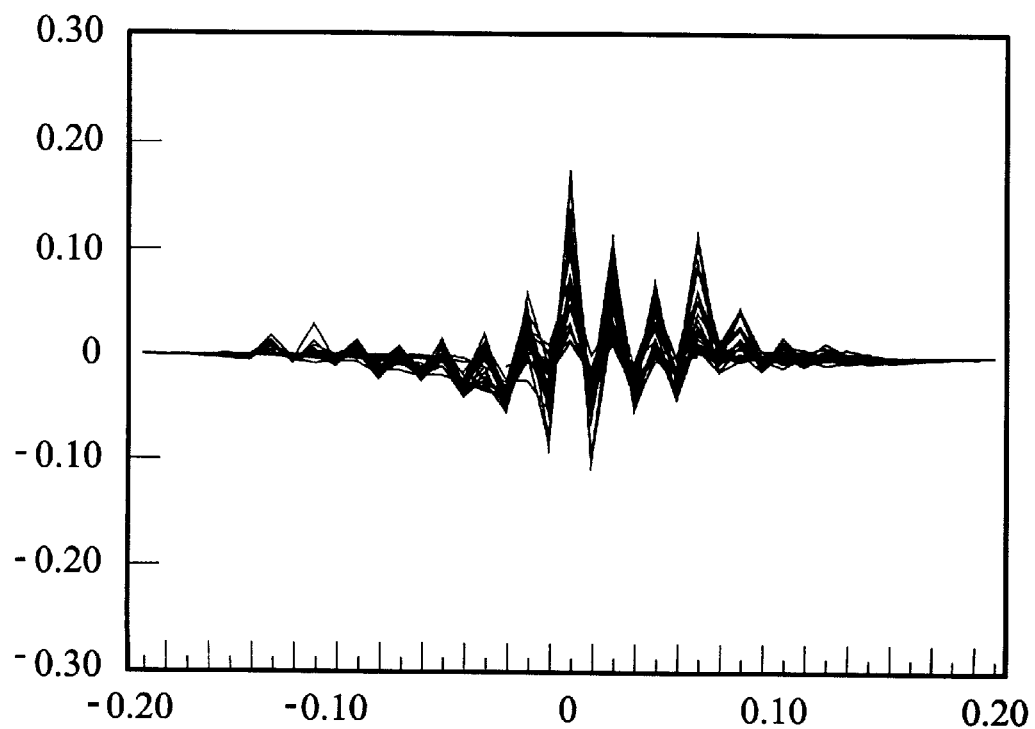
FIG. 8 is a graphical representation of the variance of the protein $P_1$ of the mycoplasma genitalium genome in the reading frame.

In all of the Variance information presented above except for tRNA, there is a general trend to have an overabundance of even phases and an underabundance of odd phases on all step lengths. This remarkable regularity could take place if almost all the phase triplets are even, but as seen in the Human T-Cell, even when there are a large number of odd phase steps the same long range behavior exhibits itself. The other possibility, and the one Nature has chosen, is that within the reading frame (3$\bar{3}$+2) odd phase triplet occur in pairs, which we call 'phase locking' so that when two odd triplets are summed over, an even phase results. For example, in protein $P_1$ in MG in the reading frame, if one triplet has an odd phase, then one of the two subsequent triplets also has an odd phase. Of the 267 phase triplets in the reading frame in $P_1$ there are 37 pairs of odd phases. All of these pairs are side by side except three odd triplets that are separated by a single even triplet. We have examined numerous protein coding regions for this phase locking and it seems to be a universal property of all the genomes we have examined. Phase locking accounts for the spiky behavior seen in all of the preceding results. FIG. 8 shows the variance of protein $P_1$ in the reading frame. FIG. 8 has the same behavior seen in FIG. 4a with three times the magnitude making it a protein coding on the forward strand of DNA.

In FIG. 8, the x-axis is the phase step for all step lengths and the y-axis is the amount each phase differs from a pure binomial. This graph shows a single protein of length 801 bps in the phase reading frame. The same structure for proteins coding on the forward strand shown in FIG. 4a occurs for this single coding region with the off frame noise removed.

Referring now to FIGS. 1a, 1b, 1c, 1d and 1e, the reading frame and its direction is produced by processing the anti-symmetric phase matrix A by calculating the RMS variance from a suspected protein coding sequence where expected statistical deviation, σ, is calculated yielding confidence level of protein section, and by calculating the magnitude of the elements $A_{ij}$ to identify direction of coding sections and tRNA sites; processing the symmetric phase matrix S by calculating the RMS variance from a suspected protein coding sequence where the expected statistical deviation, σ, is calculated yielding confidence level of protein sequence by calculating the magnitude of the elements $S_{ij}$ to measure the strength of the protein signal; and processing intra-step length comparisons by comparing step length matrices (both symmetric and anti-symmetric) for different step lengths 3$\bar{3}$; assigning statistical value to step lengths not 3$\bar{3}$, i.e., either 3$\bar{3}$+1 or 3$\bar{3}$+2; and using this information to determine the reading frame.

It was determined experimentally that the reading frame is the 3$\bar{3}$+2 frame. This means that a phase triplet starts from the last bp on one amino acid and measures the three phases from this point. The 64 possible bp triplets code 20 amino acids plus starts and stops. This redundancy factor (which is as high as 6) allows an enormous variety of bp sequences to code the same protein. Eight amino acids can be coded (alanine, arginine, glycine, leucine, proline, serine, threonine, valine) that have complete freedom as to what the final bp will be. For example, the four bp combinations (CCA,CCT,CCC,CCG) all, code for proline. Lets say the last bp on the previous amino acid is T, then we have −1 for the sum of the first two phases of proline. This means that since the first two phase steps are set, by a suitable choice of the final bp, the above four combinations respectively yield a total phase of (−2, 0, −1, −1) respectively. Therefore the freedom is there to phase lock this site. There are ten amino acids that have at least a two bp choice. For each of these, the final bp is either (A or G) or (T or C). Since the phase going to one of these is even and one odd, the choice can be made to phase lock the two triplets with this amino acid. The last two possibilities where phase locking might not be able to occur immediately following an unlocked odd phase triplet are for methionine (Met) and tryptophan (Trp). Each of these have only a single bp coding given by ATG for Met and TGG for Trp. If an odd phase triplet occurs with the last bp either C or G then all possible phases for Trp and Met are even. Therefore phase locking cannot occur immediately after the first odd phase triplet. Since both of these amino acids end in G, the only way phase locking would not be physically possible over multiple triplet coding regions is if a long strand of Met and Trp immediately followed an odd phase triplet. Since the percentages for Met and Trp are the lowest of all amino acids (approximately 1% and 2% respectively), long strands where phase locking cannot occur are very rare.

Phase locking of the odd phase triplets does give exactly the long-range order seen earlier for protein $P_1$; for this single protein the variance in the reading frame is graphed in FIG. 8. Unlike FIG. 4, this graph shows one protein with the off-sequence phases removed because of the identification of the reading frame. At this shortest length scale, phase locking and the determination of the reading frame make it possible to examine a stretch of DNA and predict the location of proteins on it irrespective of whether the proteins have ever been seen biochemically. Phase locking is not the entire story, the asymmetry of the variance on both strands as well as the genome particular coding algorithm within this framework must be understood to completely understand this mechanism. We are currently developing a program to analyze genome information and predict protein sites. With this information, several more subtle aspects of the coding onto the DNA helix can be examined.

Figure 9:
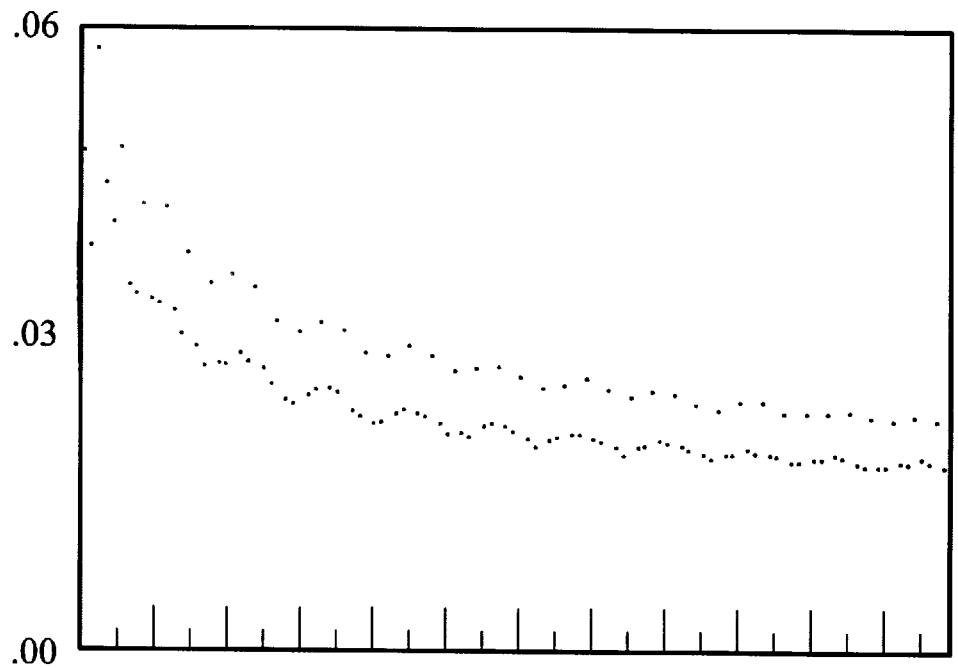
FIG. 9 is a graphical plot of the data for the mycoplasma genitalium genome as presented in FIG. 2 without connecting lines and over a larger step link spread.

Let us now return to FIG. 2 for some final observations. As well as the enhancement at step lengths divisible by 3, there is also a statistically significant overall oscillation with a frequency of approximately 11 base pairs. FIG. 9 plots the MG data from FIG. 2 without the connecting lines and over a larger step length spread. In FIG. 9, the x-axis is the number of base pairs n counted over and the y-axis is the root mean square variance from a pure binomial of size $2^{2n}$; and the genome MG is displayed showing the 11 bp oscillation over the RMS variance step length information. This oscillation could represent structural features of the DNA helix. When multiple coding regions of complete genomes are analyzed with the off frame phase information removed, this structure will be more apparent and may provide information useful in the study of DNA-protein interactions.

We have examined DNA phase information on several length scales and the particular information each such length scale provides. First, information for the whole genome was presented. At this level, phase triplet effects dominate genomes that have a large coding to non-coding percentage. It is important to note the RMS variance for all three of the yeast graphs in FIG. 2 lie approximately on top of each other. This suggests that the coding algorithm employed by the DNA may not vary much within a species. Next, the phase signature for multiple coding regions of tRNA and proteins was presented and we saw reading frame enhancement and chirality associated with coding direction.

Example 3 demonstrated how to determine the reading frame. Another major result of this section is that 'phase locking' accounts for much of the long and short range behavior shown throughout this entire paper. The long-range order seen throughout all the genomes we have examined is due in part to 'phase locking' where odd phase triplets in the reading frame come in pairs almost always adjacent. Of particular interest is the inverted signature at one step length for the Human T-Cell (as well as the Human X-Chromosome). Remarkably this does not effect the behavior on any other step lengths.

Figure 10:
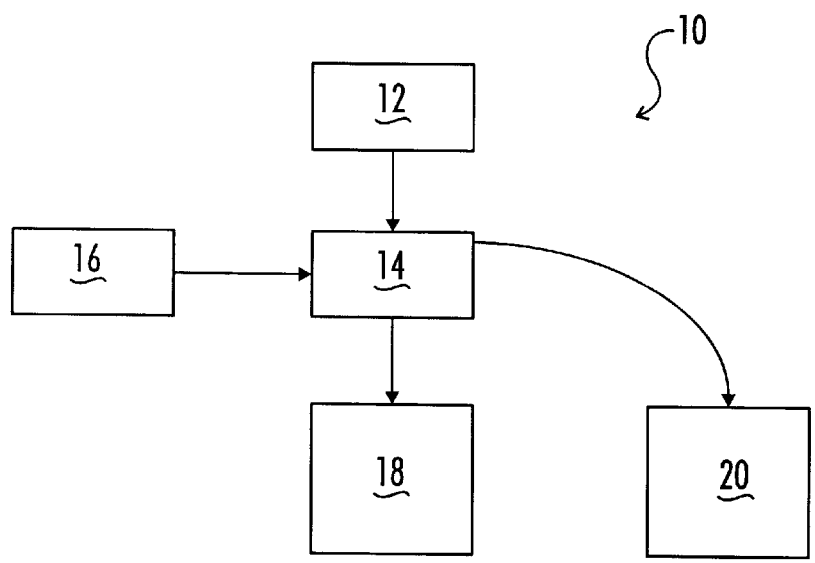
FIG. 10 depicts a schematic of the genetic information identification system of this invention.

Referring now to FIG. 10, the system of this invention is referred to generally at 10. In the exemplar system 10, a computer program more fully characterized in the source code appendix attached hereto is stored in a storage unit 12 such as a dynamic read-write memory (RAM), a read-only memory (ROM), magnetic or optical disk, or other suitable storage. A storage unit 12 is in turn associated with processing apparatus 14 such as a programmable central processing unit (CPU), a programmable read-only memory (PROM) or hardwired discrete logic circuitry.

A polynucleotide sequence generating apparatus 16 is associated with calculating apparatus 14. Polynucleotide sequence generator 16 can be in the form of an on-line database connected which is associated with processing apparatus 14 by a modem; any of the many well known DNA sequencing devices; or other database structure. Display monitor 18 and printer 20 are also associated with processing apparatus 14.

Accordingly, when processing apparatus 14 receives polynucleotide sequence signals from polynucleotide sequence generator 16, processing apparatus 14 then receives instructions from the source code embodied in storage unit 12 to characterize base changes within the sequence signals by assigning a value to each base change. The processing apparatus 14 then extracts genetic information by processing the values assigned to each base change within the sequence, also according to instructions provided from the source code embodied in storage unit 12. The processing of the values assigned to the base pair change produces genetic information from the polynucleotide sequence. An example of the processing is the calculation of the route mean square variance from a binomial distribution of the polynucleotide base signals received from generator 18.

Processing apparatus 14 then communicates the genetic information to the user of the system 10 either in the form of a graphical display as evidenced by FIGS. 1–9 attached hereto which can be displayed on monitor 18; or which can be displayed by printing them on printer 20. As more fully described herein, the presence of distinct peaks indicating significant variance from the randomness associated with a pure binomial distribution indicates the presence of genetic information, such as a protein encoding region.

The source code stored in storage unit 12 can also be adapted by one having ordinary skill in the art to produce a listing of the bases along the polynucleotide sequence that bear the genetic information. Stated differently, the processing apparatus 14 can generate the specific sequence information in terms of a base listing either to monitor 18 or to printer 20 so that the user will have the appropriate sequence that includes the genetic information.

From the sequence information which includes the genetic information, further characterization of the genetic information can be accomplished by the use of many well known techniques, including additional computer program applications. For example, if the genetic information includes the identification of a protein encoding region along the polynucleotide sequence, the encoding sequence can then be transformed into the corresponding polypeptide sequence using the table of genetic code as attached hereto as FIG. 11. Thus, the user of system 10 can proceed rapidly from the raw polynucleotide sequence data signals generated by generator 16 to a discrete polypeptide sequence.

Additionally, system 10 can be adapted to include additional source code whereby processing apparatus 14 can determine the secondary, tertiary and quaternary structures of the polypeptide sequence that is calculated from the polynucleotide sequence data signals that are generated by generator 16.

Examples of the preferred calculating apparatus include an IBM compatible computer which includes a Pentium processor and preferably operates at a frequency of 133 megahertz or more. Thus, it is contemplated that storage unit 12, processing apparatus 14 and polynucleotide sequence data generator 16 could be included within a single computer.

Figure 13:
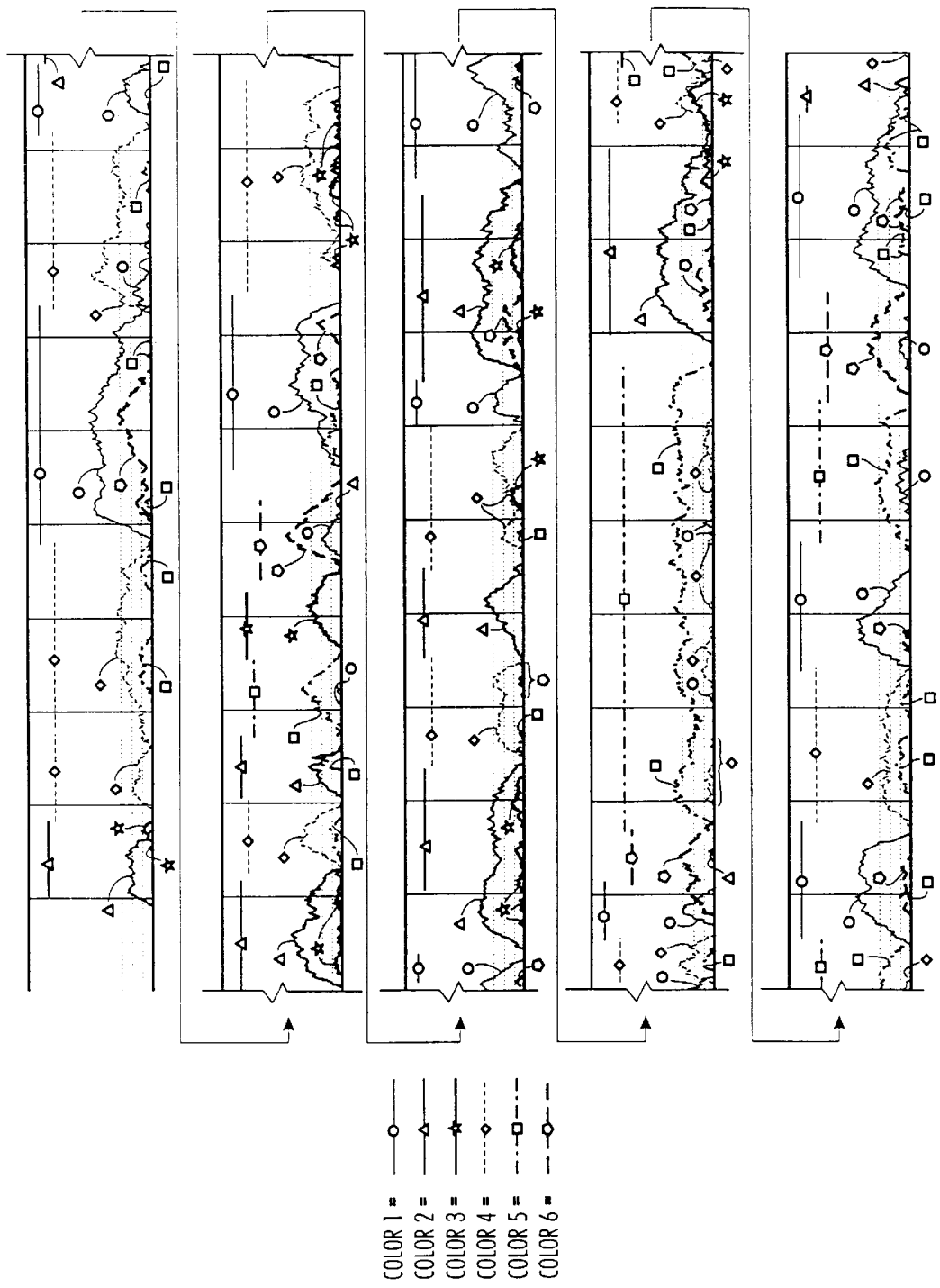
FIG. 13 depicts the results (three continuous two-color lines) of when the method and system of the present invention is applied to the first 50,000 base pairs of the organism Mycoplasma G. For comparison the horizontal bars represent known coding regions. The six colors represent the three reading frames in the forward DNA strand and the three reading frames on the complementary strand.

FIG. 13 depicts the results (three continuous two-color lines) of when the method and system of the present invention is applied to the first 50,000 base pairs of the organism Mycoplasma G. The six colors represent the six reading frames (3 Forward and 3 on the conjugate DNA strand). The vertical scale measures the strength of the phase signal on a log scale (the horizontal lines are a factor of ten apart). For comparison, the horizontal bars indicate the known location of protein coding regions extracted from GENBANK. Thus, the accuracy of the method and system of this invention is demonstrated by the correlation between the peaks on the continuous lines and the horizontal lines that represent known protein coding regions.

Thus, although there have been described particular embodiments of the present invention of a new and useful method and system for identification of genetic information from a polynucleotide sequence, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. A method of identifying genetic coding regions in an isolated polynucleotide sequence comprising the steps of:
   a) entering the polynucleotide sequence into a data processing system;
   b) identifying base changes in the polynucleotide sequence and assigning an observed base change value to each base change;
   c) transferring the observed base change values to a rate of change matrix;
   d) generating a distribution of the observed base change values from the rate of change matrix;
   e) comparing the distribution of the observed base change values to expected base change values in a statistically random biologically weighted distribution to determine one or more variances; and
   f) displaying the variances, which correspond to the genetic coding regions, to identify those genetic coding regions.

2. The method according to claim 1 wherein the variances are determined by calculating the root mean square variance of the distribution.

3. The method according to claim 1 wherein the rate of change matrix comprises a symmetric phase matrix.

4. The method according to claim 1 wherein the rate of change matrix comprises an anti-symmetric phase matrix.

5. The method according to claim 1 wherein the rate of change matrix comprises:
   a) a symmetric phase matrix, and
   b) an anti-symmetric phase matrix.

6. A method of identifying protein-coding regions in an isolated polynucleotide sequence comprising the steps of:
   a) entering the polynucleotide sequence into a data processing system;
   b) analyzing the polynucleotide sequence by identifying observed base changes and categorizing the observed base changes by assigning an observed base change value to each observed base change and transferring the observed base change values into a rate of change matrix;
   c) comparing the observed base change values assigned to each observed base change in the rate of change matrix over multiple step lengths to identify correlations in patterns of base change values over multiple step lengths;
   d) comparing the distribution of the observed base change values to expected base change values of a statistically random but biological weighted distribution to identify one or more variances; and
   e) displaying the polynucleotide sequence as a graphic display of the variances, thereby indicating the location of the protein coding regions.

7. A method of identifying an open reading frame in an isolated polynucleotide sequence, the method comprising the steps of:
   a) entering the polynucleotide sequence into a data processing system;
   b) identifying observed base changes in the polynucleotide sequence, assigning a base change value to each observed base change, and transferring the base change values to an anti-symmetric phase rate of change matrix and to a symmetric phase rate of change matrix;
   c) processing the anti-symmetric phase matrix by calculating a root mean square variance of observed base pair changes from expected random base pair changes;
   d) processing the symmetric phase matrix by calculating a root mean square variance of observed base pair changes from expected random base pair changes where the expected statistical deviation is calculated yielding a confidence level of protein sequence by calculating a magnitude of elements in the symmetric phase matrix to measure a protein signal strength;
   e) processing intra-step length comparisons by comparing both symmetric and anti-symmetric step length matrices for different step lengths Nmod 3;
   f) assigning a statistical value to step lengths not Nmod 3 to determine locations of an open reading frame; and
   g) graphically displaying the identified open reading frames in the polynucleotide sequence.

8. The method of claim 7 wherein calculating the root mean square variance further comprises calculating an expected statistical deviation to identify the directionality of the coding sections using the magnitude of elements in the anti-symmetric phase matrix.

9. The method of claim 7 wherein step lengths not Nmod 3 comprise step lengths Nmod 3+1.

10. The method of claim 7 wherein step lengths not Nmod 3 comprise step lengths Nmod 3+2.

* * * * *